(12) United States Patent  (10) Patent No.: US 7,108,423 B2
Schmitt  (45) Date of Patent: Sep. 19, 2006

(54) MULTILEAF COLLIMATOR FOR AN X-RAY DIAGNOSTIC DEVICE

(75) Inventor: Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 15 days.

(21) Appl. No.: 11/064,753

(22) Filed: Feb. 24, 2005

(65) Prior Publication Data
US 2005/0190890 A1 Sep. 1, 2005

(30) Foreign Application Priority Data
Feb. 26, 2004 (DE) .................... 10 2004 009 897

(51) Int. Cl.
*A61B 6/08* (2006.01)
(52) U.S. Cl. ..................... 378/206; 378/147
(58) Field of Classification Search ............... 378/145, 378/147, 149, 150, 151, 152, 205, 206
See application file for complete search history.

(56) References Cited

U.S. PATENT DOCUMENTS 4,167,675 A * 9/1979 Stodberg et al. .......... 378/153
5,923,725 A 7/1999 Reiff et al. ................ 378/162
6,036,362 A 3/2000 Schmitt ..................... 378/206

FOREIGN PATENT DOCUMENTS

DE  24 24 619   11/1975
DE  34 36 866 C2  4/1986

* cited by examiner

*Primary Examiner*—Courtney Thomas

(57) ABSTRACT

A multileaf collimator (1) of an X-ray diagnostic device has a housing (2) that is provided for the passage of an X-ray beam (S), collimator leaves (3) arranged in said housing for limiting the X-ray beam (S), and a light source (5) and a mirror (4) for identifying the X-ray beam (S) by visible light. A plurality of collimator leaves (3) at a time are arranged in front of the mirror (4) and behind the mirror (4) in the direction of radiation (R) of the X-ray beam (S), and are rigidly coupled together, the individual collimator leaves (3) each being arranged in collimation planes ($E_1$–$E_{14}$) which are orientated at least approximately normal to the direction of radiation (R) of the X-ray beam (S).

15 Claims, 1 Drawing Sheet

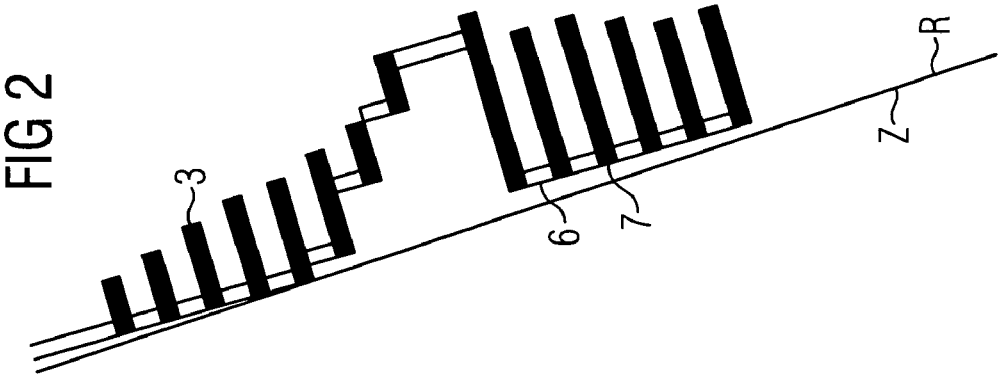
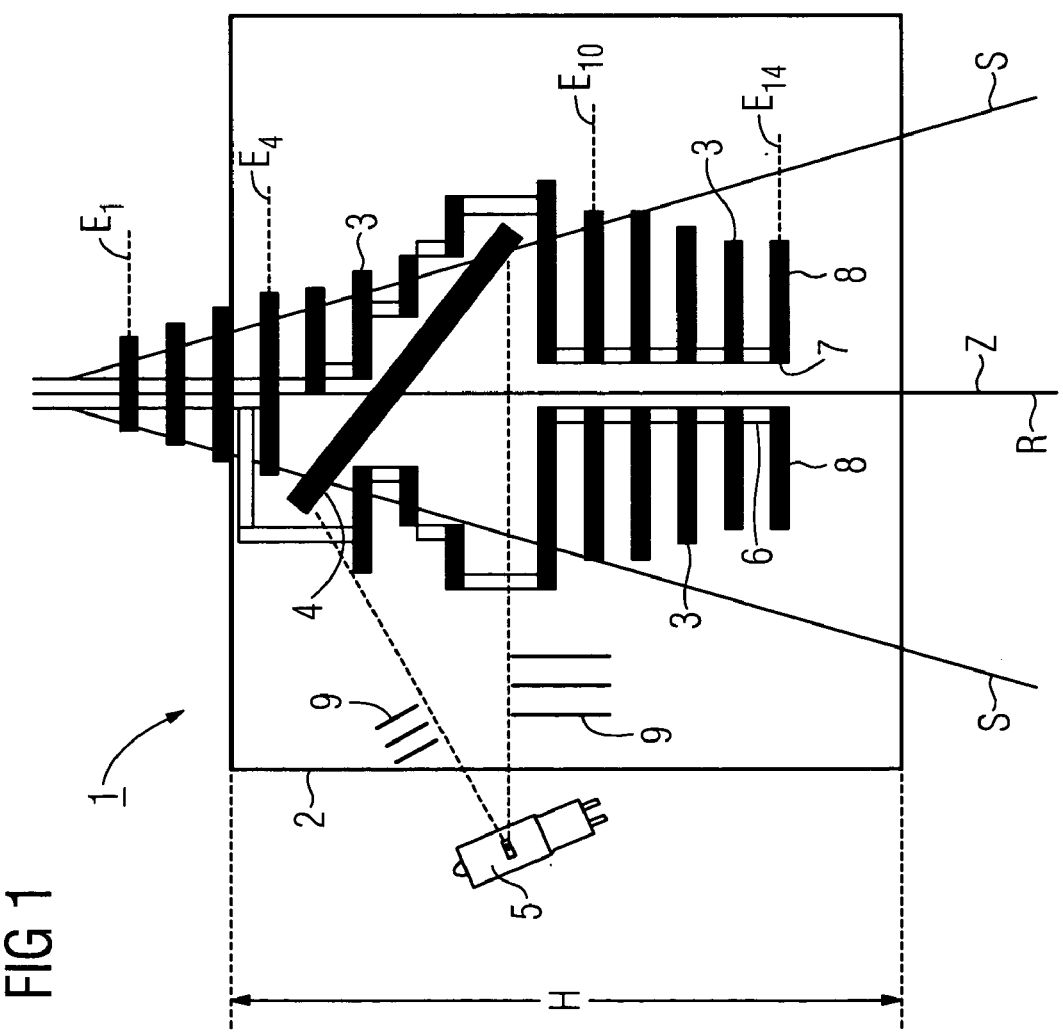

MULTILEAF COLLIMATOR FOR AN X-RAY DIAGNOSTIC DEVICE

CROSS REFERENCE TO RELATED APPLICATIONS

This application claims priority to the German application No. 10 2004 009 897.2, filed Feb. 26, 2004 which is incorporated by reference herein in its entirety.

FIELD OF INVENTION

The invention relates to a multileaf collimator provided for an X-ray diagnostic device, an X-ray beam emitted from an X-ray source being limited by collimator leaves arranged in a housing of the multileaf collimator. The multileaf collimator also contains a mirror that can receive visible light from a light source and hence enables an identification of the X-ray beam. Such a multileaf collimator is known, for example, from DE 34 36 866 C2 or DE 24 24 619 A1.

BACKGROUND OF INVENTION

The multileaf collimator known from DE 34 36 866 C2 comprises a plurality of pairs of collimator leaves coupled by means of various gears, and its overall mechanical design is complex. Tilting collimator leaves are located in the beam path of the X-ray beam both in front of and behind the mirror arranged in the multileaf collimator housing.

SUMMARY OF INVENTION

An object of the invention is to provide a multileaf collimator for an X-ray diagnostic device that exhibits a particularly good balance between design complexity, physical size and technical beam properties.

This object is achieved by the claims. This multileaf collimator for an X-ray diagnostic device has a housing, through which an X-ray beam can pass, in which are located a plurality of collimator leaves for limiting the X-ray beam, and a mirror. The mirror is provided for receiving light from a light source which is not necessarily located within the housing, and enables the X-ray beam to be identified by visible light. Individual collimator leaves or collimator-leaf pairs each define a collimation plane that is orientated at least approximately normal to the direction of radiation of the X-ray beam. Collimator leaves, mounted in the housing of the multileaf collimator so that they can tilt, are preferably provided, in particular to enable focused collimation, a plurality of collimator leaves at a time being rigidly coupled together. The collimation planes preferably extend over more than half the height of the multileaf collimator housing, the height of the housing being measured in the direction of radiation, i.e. normal to the collimation planes. At least some of the collimator leaves, preferably all the collimator leaves, are capable of focused tilting or displacement at least approximately in the respective collimation plane in order to enable an adjustable masking of part of the X-ray beam.

In a preferred embodiment, at least four collimation planes in each case are located in front of or behind the mirror in the direction of radiation of the X-ray beam, in particular both on the side of the mirror facing the X-ray source, i.e. on the focus side, and on the side facing away from the X-ray source. Collimation in multiple planes, in total preferably in at least eight planes, for example in at least ten planes, has the advantage in particular of also being a highly effective means of filtering out secondary and tertiary radiation.

In a way that is advantageous to produce, the collimator leaves are preferably manufactured as moldings or castings, in particular from a light alloy. For beam screening purposes, the edges of the collimator leaves can be lead coated. Steel can also be used as the material for the collimator leaves. Alternatively, the collimator leaves can also be made of a plastic that contains, in order to increase the beam absorption, an element suitable for the purpose, preferably barium. Regardless of what material or materials the collimator leaves are made of, preferably a plurality of collimator leaves, some of which are arranged in front of the mirror and some behind the mirror with respect to the X-ray beam path, form a rigid molding or casting which is mounted in the housing so it can move as a whole. Preferably four such moldings or castings interleave with their individual collimator leaves in such a way that a rectangular radiation cross-section of the X-ray beam can be set up.

The described beam-limiting design employing collimator leaves that can be displaced and/or tilted, which is easy to produce, saves weight and space and requires minimum control complexity, can also be applied analogously to the light beam provided for identifying the X-ray beam.

According to the principle known from DE 34 36 866 C2 or U.S. Pat. No. 6,036,362, for example, beam filters can also be integrated in the housing of the multileaf filter in addition to the collimator leaves or in place of individual collimator leaves. In addition, or alternatively, an iris aperture can also be provided, preferably integrated in the housing.

Both the collimator leaves and, if applicable, the additional beam filters and/or additional leaves preferably have motorized adjustment. In addition, according to an advantageous development, the collimator leaves can be designed in such a way that the edge region of a collimator leaf, said region being used for limiting the X-ray beam, is also provided for producing a machine- or component-specific identification on the X-ray photograph, as known in principle from U.S. Pat. No. 5,923,725, for example. The compact design of the multileaf filter is retained even when including one or more of the additional features cited. Unlike a multileaf filter having solely tilting collimator leaves, these leaves can also be replaced far more easily.

BRIEF DESCRIPTION OF THE DRAWINGS

An exemplary embodiment of the invention is described in more detail below with reference to a drawing, in which in highly simplified representation, FIG. 1 shows schematically a cross-section of a multileaf collimator of an X-ray diagnostic device, and FIG. 2 shows a section of the multileaf collimator of FIG. 1 through another cross-section.

Corresponding parts are labeled in each figure with the same reference numerals.

DETAILED DESCRIPTION OF INVENTION

A multileaf collimator 1 shown symbolically in FIGS. 1 and 2 for a medical X-ray diagnostic device (not shown in further detail) comprises a housing 2, a plurality of collimator leaves 3, mostly arranged in pairs, a mirror 4 and a light source 5. The X-ray beam emitted from an X-ray source (not shown) is labeled with S, and the direction of radiation with R. In the cross-section shown in FIG. 1, the multileaf collimator 1, with the exception of the mirror 4, has a substantially symmetrical structure about the straight line given by the direction of radiation R. A light beam, indicated by dashed lines, emitted by the light source 5, is reflected by the mirror 4, which is effectively transparent to X-rays, thereby identifying by visible light the area to be examined by means of the X-ray beam S, in particular a patient to be examined. The multileaf collimator 1 is not restricted to medical applications, however, but can also be used in the field of material testing for example.

The individual collimator leaves 3 are located in a plurality of collimation planes, in the exemplary embodiment fourteen collimation planes $E_1$ to $E_{14}$, orientated normal to the direction of radiation R. Connecting webs 6 lie between the collimator leaves 3 of the various collimation planes $E_1$ to $E_{14}$. Most of the collimator leaves 3 are arranged inside the housing 2, whose height is labeled H, although some are also arranged on the focus side i.e. on the side outside the housing 2 facing the X-ray source.

The collimation planes $E_1$ to $E_{14}$ approximately fill the complete height H of the housing 2. In general, a beam S having a rectangular cross-section is formed by means of the collimator leaves 3, which are orientated not necessarily exactly with the collimation planes $E_1$ to $E_{14}$ but which enclose with said planes an acute angle, for example, in particular an angle of less than 30°, the collimator leaves 3 shown in the diagrams each limiting either the width or height of the rectangle. For particularly effective and sharp limiting of the beam S, at least some of the edges 7 of the collimator leaves 3 are lead coated.

A plurality of collimator leaves 3 connected with connecting webs 6 are produced as a single light-alloy casting, in particular an aluminum casting. A total of four light-alloy castings, referred to in general as a casting 8, form the totality of collimator leaves 3, where pairs of castings 8 are arranged approximately symmetrically about the straight line given by the direction of radiation R, also referred to as central beam Z, and limit the height or width of the beam S. Motorized adjustment of each pair of opposite castings 8 approximately linearly across the central beam Z, normal to the direction of radiation R, is possible in order to the adjust the height or width of the beam S. Preferably, an exactly linear adjustment capability of the castings 8 is not provided, but a tilting capability such that in every position the collimator leaves 3 are adjusted give a focused beam S, referred to for short as a focused tilting capability. Each self-rigid molding or casting 8 comprises in the direction of radiation R, both in front of and behind the mirror 4, a plurality of collimator leaves 3.

In a similar way to the collimator leaves 3 that limit the X-ray beam S, a collimating device 9 is arranged between the light source 5 and the mirror 4 in order to influence the light beam emitted from the light source 5. The collimating device 9 is adjusted automatically, synchronously with the adjustment of the collimator leaves 3, also referred to as the main collimation.

As can be seen in particular from FIG. 1, two opposite castings 8, which alternatively can also be made, for example, of plastic filled with element that absorbs X-rays, in particular barium, describes in the cross-section shown approximately the shape of a tree. The collimator leaves 3 limiting the height of the beam S on the one hand and its width on the other, are interleaved with each other in such a way as to produce a multi-layer screening effect which effectively eliminates in particular secondary and tertiary radiation. Despite its simple mechanical design comprising few moving parts, the multileaf collimator 1 thus has particularly good physical properties and is a major contributory factor in producing an exactly defined beam S.

The invention claimed is:

1. A multi-leaf collimator for an X-ray diagnostic device, comprising:
   a housing sized and configured for an X-ray beam, the X-ray beam comprising a central portion and divergent portions passing through the housing;
   a plurality of self-rigid sets of collimator leaves arranged within the housing for narrowing the X-ray beam, wherein each of the self-rigid sets is disposed on only one side of the central portion of the X-ray beam generally opposite another one of the self-rigid sets of collimator leaves disposed on the opposite side of the central portion of the X-ray beam; and
   a light source adapted to emit a visible light beam that crosses the X-ray beam in a beam crossing space and a mirror disposed in the beam crossing space for reflecting the visible light beam in line with the X-ray beam for highlighting the X-ray beam using the visible light, wherein a first part of each self-rigid set of collimator leaves is arranged in front of and a second part of each self-rigid set of collimator leaves is arranged behind the mirror relative to an emitting direction of the X-ray beam, each collimator leaf arranged in a collimation plane assigned to the respective collimator leaf and the collimation planes arranged substantially perpendicular relative to the emitting direction.

2. The multi-leaf collimator according to claim 1, wherein the collimation planes extend over more than half of the height of the housing.

3. The multi-leaf collimator according to claim 1, wherein at least four of the collimation planes are arranged on a side of the mirror facing an X-ray source emitting the X-ray beam.

4. The multi-leaf collimator according to claim 1, wherein at least four of the collimation planes are located on a side of the mirror facing away from an X-ray source emitting the X-ray beam.

5. The multi-leaf collimator according to claim 1, wherein at least some of the self-rigid sets of collimator leaves are moveable relative to the central portion of the X-ray beam.

6. The multi-leaf collimator according to claim 5, wherein the moveable self-rigid sets of collimator leaves are swivel-mounted.

7. The multi-leaf collimator according to claim 5, wherein each leaf in each movable self-rigid set of collimator leaves is relocatable in the collimation plane assigned to said each leaf.

8. The multi-leaf collimator according to claim 1, wherein at least some of the self-rigid sets of collimator leaves are parts of mold or cast parts.

9. The multi-leaf collimator according to claim 8, wherein the first and second parts of at least some of the self-rigid of collimator leaves form one part of mold or one cast part, the part of mold or cast part respectively moveably supported in the housing.

10. The multi-leaf collimator according to claim 1, wherein at least some of the collimator leaves are made of metal.

11. The multi-leaf collimator according to claim 1, wherein at least some of the collimator leaves are made of plastic.

12. The multi-leaf collimator according to claim 11, wherein the plastic includes an element adapted to absorb X-ray radiation.

13. The multi-leaf collimator as claimed in claim 12, wherein the element is barium.

14. The multi-leaf collimator according to claim 1, wherein at least one collimator leaf has at least one lead-coated edge.

15. A medical X-ray diagnostic device, comprising a multi-leaf collimator, the multi-leaf collimator comprising:
- a housing sized and configured for an X-ray beam, the X-ray beam comprising a central portion and divergent portions passing through the housing;
- a plurality of self-rigid sets of collimator leaves arranged within the housing for narrowing the X-ray beam, wherein each of the self-rigid sets is disposed on only one side of the central portion of the X-ray beam generally opposite another one of the self-rigid sets of collimator leaves disposed on the opposite side of the central portion of the X-ray beam; and
- a light source adapted to emit a visible light beam that crosses the X-ray beam in a beam crossing space and a mirror disposed in the beam crossing space for reflecting the visible light beam in line with the X-ray beam for highlighting the X-ray beam using the visible light, wherein a first part of each self-rigid set of collimator leaves is arranged in front of and a second part of each self-rigid set of collimator leaves is arranged behind the mirror relative to an emitting direction of the X-ray beam, each collimator leaf arranged in a collimation plane assigned to the respective collimator leaf and the collimation planes arranged substantially perpendicular relative to the emitting direction.

* * * * *